United States Patent [19]

Klausener et al.

[11] Patent Number: 5,235,087
[45] Date of Patent: Aug. 10, 1993

[54] PROCESS FOR THE PREPARATION OF DIALKYL CARBONATES

[75] Inventors: Alexander Klausener, Stolberg; Heinz Landscheidt, Duisburg; Heinz U. Blank, Odenthal-Gloebusch; Walter Kipshagen, Leverkusen, all of Fed. Rep. of Germany

[73] Assignee: Bayer Aktiengesellschaft, Leverkusen, Fed. Rep. of Germany

[21] Appl. No.: 717,948

[22] Filed: Jun. 20, 1991

[30] Foreign Application Priority Data

Jun. 30, 1990 [DE] Fed. Rep. of Germany ....... 4020941

[51] Int. Cl.$^5$ ..................... C07C 69/96; C07C 67/36
[52] U.S. Cl. .................... 558/260; 558/270; 560/204
[58] Field of Search ................. 558/260, 277; 560/204

[56] References Cited

U.S. PATENT DOCUMENTS 4,473,705  9/1984  Miyamori et al. ................. 560/193
4,629,806  12/1986  Cleveland et al. ................. 560/204

FOREIGN PATENT DOCUMENTS 0057629  8/1982  European Pat. Off. .
0354970  2/1990  European Pat. Off. .
0365083  4/1990  European Pat. Off. .
0425197  5/1991  European Pat. Off. .
60-181051  9/1985  Japan .
2003872  3/1979  United Kingdom .

OTHER PUBLICATIONS

Ullmann's Encyclopedia of Industrial Chemistry vol. A5 (1986), 197–202.
CA 104 (1986)110355t.

Primary Examiner—Jose G. Dees
Assistant Examiner—Joseph M. Conrad
Attorney, Agent, or Firm—Sprung Horn Kramer & Woods

[57] ABSTRACT

Dialkyl carbonates can be prepared by reacting carbon monoxide with alkyl nitrites over a modified platinum metal supported catalyst at an elevated temperature in a continuous gas phase reaction, the reaction being carried out with the exclusion of additional oxidizing substances and, if appropriate, the presence of a lower alcohol.

20 Claims, No Drawings

PROCESS FOR THE PREPARATION OF DIALKYL CARBONATES

BACKGROUND OF THE INVENTION

1. Field of the Invention

The invention relates to a new process for the preparation of dialkyl carbonates by reacting carbon monoxide with alkyl nitrites in a continuous gas phase reaction over a catalyst.

Dialkyl carbonates are of general chemical importance. Thus, for example, diethyl carbonate is an excellent solvent in the middle boiling range. Furthermore, the dialkyl carbonates are excellent carbonylation and alkylation reagents. Finally, they have acquired great importance in the preparation of other carbonates and of urethanes and ureas.

2. Description of the Related Art

Various methods for the preparation of dialkyl carbonates are described in the literature. In this regard reactions of phosgene or alkyl chloroformates with alcohols (Ullmann's Encyclopaedia of Industrial Chemistry, Vol. A 5 (1986), 197-202) have been of considerable industrial importance up to the present time. There is, however, an increasing interest in replacing, by other processes, the use of phosgene, which is toxic, or of the intermediate products derived therefrom, such as chloroformic acid esters. Thus the preparation of dialkyl carbonates by reacting carbon monoxide with lower alcohols in the presence of various catalysts and co-catalysts is known. In accordance with EP 365,083 lower alcohols are reacted with carbon monoxide in the presence of oxygen over a catalyst system composed of a copper alkoxyhalide and water. In accordance with EP 354,970 lower alcohols are also reacted with carbon monoxide in the presence of oxygen over a catalyst system consisting of a combination of a copper catalyst or a platinum metal catalyst and an alkaline earth compound, both the copper and the platinum metal and also the alkaline earth metal being employed in the form of a salt of a weak acid or in the form of a halide.

The reaction of an alkyl nitrite with carbon monoxide in the gas phase over a supported platinum metal catalyst is disclosed in JP 60-181, 051 (1985) (C.A. 104 (1986, 110 355 t)), the reaction being carried out in the presence of 10 mol %, relative to CO, of an oxidizing agent, for example oxygen. Furthermore, it is disclosed in EP 57,629 that an alkyl nitrite, which is prepared in situ from the appropriate alcohol and an oxide of nitrogen, is reacted with CO in a gas phase process in the presence of a supported palladium catalyst to give a dialkyl oxalate.

SUMMARY OF THE INVENTION

The aim was to have available a continuous gas phase process for the preparation of dialkyl carbonates which can be carried out without additional oxidizing substances which, in the presence of a catalyst and at an elevated temperature, result in every case in an ignitable mixture, which cannot, from the point of view of industrial safety, be introduced into large-scale industrial production. It must also be assumed that the additional oxidizing substance converts a considerable part of the CO into $CO_2$ in an undesired manner, which must lead to serious losses in yield.

A process has been found for the preparation of dialkyl carbonates of the formula $$O=C(OR)_2 \qquad (I),$$

wherein
R denotes linear or branched $C_1$-$C_4$-alkyl,
by reacting carbon monoxide with alkyl nitrites of the formula $$RONO \qquad (II)$$

wherein
R has the meaning indicated above, in the presence of an inert gas over a supported platinum metal catalyst at an elevated temperature and in a continuous gas phase reaction, which process is characterised in that the reaction is carried out with the exclusion of additional oxidizing substances and with or without the addition of an alcohol of the formula $$ROH \qquad (III)$$

wherein
R has the meaning indicated,
a supported platinum metal catalyst being employed, which has been modified by one or more elements belonging to the group consisting of iron, cobalt, nickel, copper, lead, molybdenum, tungsten, vanadium, tin, bismuth, sulphur, selenium, tellurium, gold, antimony and arsenic in an amount of 0.01 to 8 % by weight, relative to the total weight of the catalyst.

DETAILED DESCRIPTION OF THE INVENTION

The reaction in the process according to the invention takes place as shown in the equation below:

$$CO + 2\ RONO \rightarrow O=C(OR)_2 + 2\ NO.$$

The process according to the invention gives high conversions of the carbon monoxide (CO) introduced into the reaction and also high selectivities of conversion to the desired dialkyl carbonates, which could not have been expected from a knowledge of the known gas phase reactions. Thus only a small fraction of the carbon monoxide employed is converted into the undesired carbon dioxide. In accordance with the invention, the corresponding dialkyl oxalates are formed, as further valuable products, besides the dialkyl carbonates. Compared with the state of the art, the sum of the dialkyl carbonates and the dialkyl oxalates gives an improved chemical yield, relative to CO converted.

Examples of linear or branched alkyl having up to 4 C atoms are methyl, ethyl, propyl, isopropyl, butyl or isobutyl, preferably the n-alkyls mentioned, particularly preferably methyl and ethyl and very particularly preferably methyl.

In principle it is possible to use as starting material a mixture of different alkyl nitrites, but then a mixture of different dialkyl carbonates and, if appropriate, unsymmetrically substituted dialkyl carbonates can also be formed. In the sense of a unitary reaction it is therefore preferable to use only one alkyl nitrite as starting material.

The alkyl nitrite is diluted with an inert gas, which then also assumes the function of a carrier gas. Any gas which is chemically stable under the reaction conditions may be mentioned as the inert gas, preferably noble gases, nitrogen and carbon dioxide, particularly preferably argon, nitrogen and carbon dioxide and very particularly preferably nitrogen and carbon dioxide. The amount of the carrier gas is about 20 to 80% by volume, preferably 30 to 70% by volume, of the total gas mixture passed over the catalyst.

The ratio by volume of CO to alkyl nitrite is 1:2-15, preferably 1:2-12 and particularly preferably 1:2-10.

The process according to the invention can be carried out with or without the addition of an alcohol of the formula (III). In the event that the process is carried out with an added alcohol, the ratio by volume of the latter to carbon monoxide is 0.1-10:1, preferably 0.2-5:1. The addition of methanol can be advantageous particularly in the preparation of dimethyl carbonate.

The process according to the invention is carried out at a temperature of 80°-200° C., preferably 90°-180° C. and particularly preferably 100°-150° C. and under a pressure of 0.8-8 bar, preferably 1-3 bar and particularly preferably 1-2.5 bar.

Suitable catalysts are supported catalysts of the platinum metal group, on their own or as a mixture of several of these. The following metals of the platinum group may be mentioned as preferable: platinum, ruthenium, rhodium, iridium and palladium; palladium is particularly preferred. The concentration of the noble metals on the support is 0.01-5 % by weight, preferably 0.05-3% by weight, relative to the total weight of the catalyst. Suitable supports are any supports which are otherwise customary for platinum metal catalysts, for example: aluminium oxides, spinels, silicates, montmorillonites, zeolites, active charcoals, molecular sieves, diatomaceous earths, silicon carbide, silicon oxide and others.

The modified platinum metal supported catalysts to be employed in accordance with the invention contain further added amounts of metals and/or metalloids and/or nonmetals in a total amount of 0.01-8% by weight, relative to the total weight of the catalyst. Examples of additives of this type are iron, cobalt, nickel, copper, lead, molybdenum, tungsten, vanadium, tin, bismuth, sulphur, selenium, tellurium, gold, antimony, arsenic and others; on their own or as a mixture of several of these, and in an elemental or combined form. Cobalt, iron, nickel, tin, lead, selenium, antimony, tellurium and sulphur, on their own or as a mixture of several of these, are preferred as additives of this type, particularly preferably in a total amount of 0.01-4% by weight, relative to the total weight of the catalyst. A suitable combined form of such added elements is, above all, the oxidic or the sulphidic form.

The preparation of such modified platinum metal supported catalysts is carried out by methods known in principle to those skilled in the art. Thus one of the supports mentioned can be impregnated or sprayed with a solution of one or more platinum metal compound(s) and also with a solution of one or more modifying additives. The platinum metals and the additives can be applied together or separately. In general, a drying process follows each impregnation; to complete its preparation the catalyst is calcined several times. Examples of compounds of the platinum metals and of the additives are the chlorides, nitrates and acetates, the ions of which are removed from the catalyst in the course of calcination. Elements in higher valency states can be employed, for example, in the form of ammonium salts (ammonium molybdate, vanadate, antimonate, arsenate and the like). Sulphur can also be applied, for example, by impregnation of organic substances (thiophene, thioethers and the like). The volume hourly space velocity over the catalyst is 1-800 l of CO, preferably 10-500 l of CO, per hour per g of noble metal on the catalyst.

The preparation of the alkyl nitrites to be employed in accordance with the invention is carried out by known processes, for example from the appropriate alcohol and nitrous acid, which is formed in situ from an alkali metal nitrite and a mineral acid (for example sulphuric acid).

The nitrogen monoxide formed in the course of the process according to the invention can be continuously regenerated by means of oxygen and fresh alcohol to give alkyl nitrite (German Offenlegungsschrift 3,834,065) and can be recycled together with unconverted carbon monoxide and unconverted alkyl nitrite.

EXAMPLE 1

A gas mixture consisting of 39% of nitrogen, 18% of methanol, 35% of methyl nitrite and 8% of carbon monoxide (% by volume) was passed, at a volume velocity of 25.5 1/h, through a glass tubular reactor (250 cm$^3$) which was heated to 125° C. and packed with Raschig rings and 20 g (25 ml) of a Pd catalyst (0.5% of Pd on Al$_2$O$_3$, doped with 0.2% of sulphur). The gas leaving the reactor was cooled, the condensed products were collected and their composition was analysed, as also was that of the gaseous, non-condensed products. A selectivity of conversion of 24% to dimethyl carbonate (DMC) and of 71% to dimethyl oxalate (DMO), relative to CO converted, was obtained. The yields, relative to CO reacted, were 13% of DMC and 40% of DMO. The space time yield (STY) of DMC was 43 g/l h.

EXAMPLES 2-8

A gas mixture consisting of 50% of nitrogen, 22.5% of methyl nitrite, 22.5% of methanol and 5% of carbon monoxide (% by volume) was passed, at a volumetric rate of flow of 20 1/h, through a tubular reactor (250 cm$^3$), which was heated at the particular temperature and packed with Raschig rings and the amount m of the particular catalyst employed The gas leaving the reactor was cooled, and the condensed samples were collected and their composition was analysed. The results are shown in Table 1.

TABLE 1

| Example of catalyst | m [g] | Selectivity of conversion, Yield relative to CO converted | | relative to CO employed | | STY DMC [g/l · h] |
|---|---|---|---|---|---|---|
| | | DMC [%] | DMO [%] | DMC [%] | DMO [%] | |
| 2  0.5% of Pd + 0.3% of CO on Al$_2$O$_3$ | 20 | 31 | 65 | 20 | 41 | 33 |
| 3  0.5% of Pd + 0.05% of S on Al$_2$O$_3$ | 20 | 43 | 51 | 17 | 20 | 26 |
| 4  0.5% of Pd + | 20 | 44 | 41 | 14 | 13 | 23 |

TABLE 1-continued

| Example of catalyst | m [g] | Selectivity of conversion, Yield relative to CO converted | | relative to CO employed | | STY DMC [g/l·h] |
|---|---|---|---|---|---|---|
| | | DMC [%] | DMO [%] | DMC [%] | DMO [%] | |
| 0.2% of S on $Al_2O_3$ | | | | | | |
| 5  0.5% of Pd + 0.05% of S on $Al_2O_3$ | 10 | 40 | 53 | 14 | 19 | 22 |
| 6  0.5% of Pd + 0.2% of S on $Al_2O_3$ | 20 | 42 | 55 | 17 | 23 | 27 |
| 7  0.5% of Pd + 0.05% of S on $Al_2O_3$ | 5 | 33 | 63 | 11 | 21 | 70 |
| 8  0.5% of Pd + 0.2% of S on $Al_2O_3$ | 10 | 38 | 42 | 15 | 17 | 50 |

What is claimed is:

1. A process having improved selectivity for the preparation of a dialkyl carbonate of the formula $$O=C(OR)_2$$

wherein

R denotes a linear or branched $C_1$-$C_4$-alkyl, by reacting carbon monoxide with an alkyl nitrite of the formula $$RONO$$

wherein

R has the meaning indicated, in the presence of an inert gas over a supported platinum metal catalyst at an elevated temperature and in a continuous gas phase reaction, wherein the reaction is carried out with the exclusion of additional oxidizing substances and with or without the addition of an alcohol of the formula $$ROH$$

wherein

R has the meaning indicated, a supported platinum metal catalyst being employed which has been modified by one or more elements belonging to the group consisting of iron, cobalt, nickel, copper, lead, molybdenum, tungsten, vanadium, tin, bismuth, sulphur, selenium, tellurium, gold, antimony and arsenic in an amount of 0.01 to 8% by weight, relative to the total weight of the catalyst.

2. The process of claim 1, wherein the alkyl nitrite or alcohol contains as the alkyl group an n-alkyl.

3. The process of claim 2, wherein the alkyl nitrite or alcohol contains, as the alkyl group, methyl or ethyl, 4. The process of claim 3, wherein the alkyl nitrite or alcohol contains, as the alkyl group, methyl.

5. The process of claim 1, wherein the inert gas employed is a noble gas, nitrogen or carbon dioxide in an amount of 20 to 80% by volume of the total gas mixture passed over the catalyst.

6. The process of claim 5, wherein the inert gas is employed in an amount of 30 to 70% by volume of the total gas mixture.

7. The process of claim 5, wherein the inert gas employed is argon, nitrogen or carbon dioxide.

8. The process of claim 7, wherein the inert gas employed is nitrogen or carbon dioxide.

9. The process of claim 1, wherein the ratio by volume of carbon monoxide to alkyl nitrite is 1:2-15.

10. The process of claim 9, wherein the ratio by volume of carbon monoxide to alkyl nitrite is 1:2-12.

11. The process of claim 10, wherein the ratio by volume of carbon monoxide to alkyl nitrite is 1:2-10.

12. The process of claim i, wherein in the event of an alcohol being concomitantly used, the ratio by volume of alcohol to carbon monoxide is 0.1-10:1.

13. The process of claim 12, wherein methyl alcohol is used concomitantly in a ratio by volume of methyl alcohol to carbon monoxide of 0.1-10:1.

14. The process of claim 12, wherein, in the event of an alcohol being concomitantly used, the ratio by volume of alcohol to carbon monoxide is 0.1-5:1.

15. The process of claim 1, which is carried out at a temperature of 80°-200° C. and under pressure of 0.8-8 bar.

16. The process of claim 15, which is carried out at a temperature of 90°-180° C.

17. The process of claim 1, wherein the platinum metal catalyst contains one or more elements belonging to the group consisting of palladium, platinum, ruthenium, rhodium and iridium, in an amount of 0.1-5% by weight, relative to the total weight of the catalyst.

18. The process of claim 17, wherein the platinum metal is palladium or iridium or a mixture of these.

19. The process of claim 1, wherein the supported platinum metal catalyst is modified by adding one or more elements belonging to the group consisting of iron, cobalt, nickel, tin, lead, selenium, antimony, tellurium and sulphur.

20. The process of claim 1, wherein the modifying elements are employed in a total amount of 0.01 to 4% by weight, relative to the total weight of the catalyst.

* * * * *

UNITED STATES PATENT AND TRADEMARK OFFICE
CERTIFICATE OF CORRECTION

PATENT NO. : 5,235,087
DATED : August 10, 1993
INVENTOR(S) : Klausener, et al.

It is certified that error appears in the above-identified patent and that said Letters Patent is hereby corrected as shown below:

Col. 6, line 31  After " claim " delete " i " and substitute -- 1 --

Signed and Sealed this

Seventh Day of February, 1995

Attest:

BRUCE LEHMAN

Attesting Officer

Commissioner of Patents and Trademarks